(12) United States Patent
Nambu

(10) Patent No.: US 11,096,640 B2
(45) Date of Patent: Aug. 24, 2021

(54) X-RAY DIAGNOSTIC APPARATUS, IMAGE PROCESSING APPARATUS, AND IMAGE PROCESSING METHOD

(71) Applicant: TOSHIBA MEDICAL SYSTEMS CORPORATION, Otawara (JP)

(72) Inventor: Kyojiro Nambu, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 683 days.

(21) Appl. No.: 15/975,210

(22) Filed: May 9, 2018

(65) Prior Publication Data

US 2018/0256124 A1    Sep. 13, 2018

Related U.S. Application Data

(62) Division of application No. 15/048,289, filed on Feb. 19, 2016, now Pat. No. 10,631,806.

(30) Foreign Application Priority Data

Feb. 19, 2015   (JP) .................................. 2015-030133
Feb. 18, 2016   (JP) .................................. 2016-028954

(51) Int. Cl.
*A61B 6/00*    (2006.01)

(52) U.S. Cl.
CPC ............ *A61B 6/481* (2013.01); *A61B 6/4441* (2013.01); *A61B 6/504* (2013.01); *A61B 6/5241* (2013.01)

(58) Field of Classification Search
None
See application file for complete search history.

(56) References Cited

U.S. PATENT DOCUMENTS 4,544,948 A * 10/1985 Okazaki ............... H04N 5/3205
                                                      348/E5.089
6,052,476 A     4/2000 Qian et al.
2004/0114717 A1* 6/2004 Kato ....................... G06T 5/007
                                                      378/62

(Continued)

FOREIGN PATENT DOCUMENTS

JP   2011-160978      8/2011
JP   2012-61307 A     3/2012

(Continued)

OTHER PUBLICATIONS

Office Action dated Aug. 12, 2019 in co-pending U.S. Appl. No. 15/048,298, citing documents AA and AB therin , 19 pages.

(Continued)

*Primary Examiner* — Yi-Shan Yang
(74) *Attorney, Agent, or Firm* — Oblon, McClelland, Maier & Neustadt, L.L.P.

(57) ABSTRACT

According to one embodiment, an X-ray diagnostic apparatus generating an X-ray image in a region of interest, includes a radiography device and processing circuitry. The radiography device takes a first X-ray image before injection of a contrast medium, and takes a second X-ray image and a third X-ray image after injection of the contrast medium. The processing circuitry generates an output image having pixel values that are ratios of pixel values between a difference between the second X-ray image and the first X-ray image and a difference between the third X-ray image and the first X-ray image.

3 Claims, 12 Drawing Sheets

(56) References Cited

U.S. PATENT DOCUMENTS

| | | |
|---|---|---|
| 2009/0034820 A1* | 2/2009 | Sugiyama ............ A61B 6/5235 |
| | | 382/132 |
| 2009/0180589 A1 | 7/2009 | Wang et al. |
| 2010/0198053 A1 | 8/2010 | Miyazaki et al. |
| 2012/0237098 A1 | 9/2012 | Rognin et al. |
| 2013/0077839 A1 | 3/2013 | Horz et al. |
| 2013/0079626 A1 | 3/2013 | Shmatukha et al. |
| 2014/0219423 A1* | 8/2014 | Bertens .................. A61B 6/482 |
| | | 378/62 |
| 2017/0251992 A1 | 9/2017 | Jang et al. |

FOREIGN PATENT DOCUMENTS

| | | |
|---|---|---|
| JP | 2014-12133 A | 1/2014 |
| JP | 2014-128648 A | 7/2014 |

OTHER PUBLICATIONS

Office Action dated Mar. 7, 2019, in co-pending U.S. Appl. No. 15/048,289.

Woong Yoon et al., "Contrast Enhancement and Contrast Extravasation on Computed Tomography After Intra-Arterial Thrombolysis in Patients With Acute Ischemic Stroke", Stroke. 2004;35:876-881. (Year: 2004).

Office Action dated Jul. 23, 2018 in co-pending U.S. Appl. No. 15/048,289, citing documents AA-AF and AX therin, 20 pages.

O'Connor, J. P. B. et al., "Dynamic Contrast-Enhanced Imaging Technique: CT and MRI" The British Journal of Radiology vol. 84, 2011, S112-S120.

Office Action dated Oct. 23, 2019 in Japanese Patent Application No. 2016-028954.

* cited by examiner

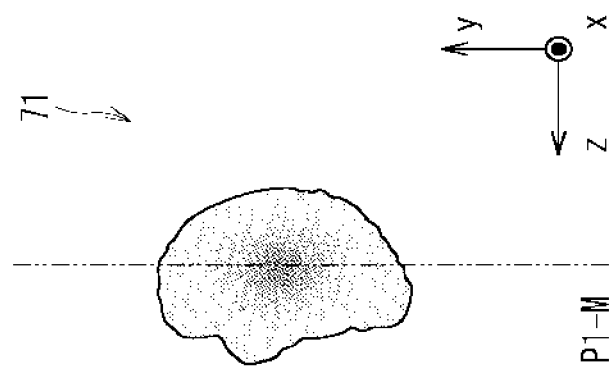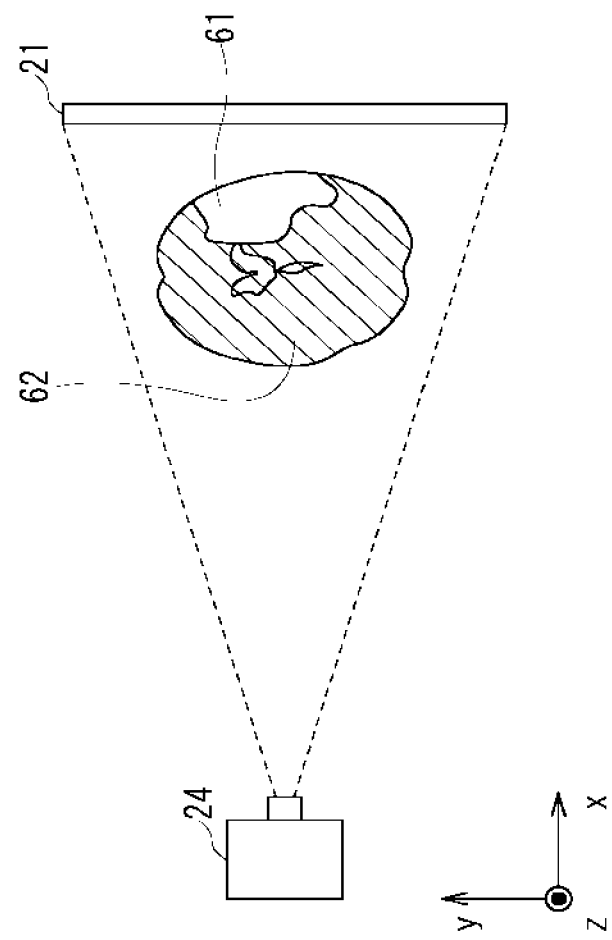

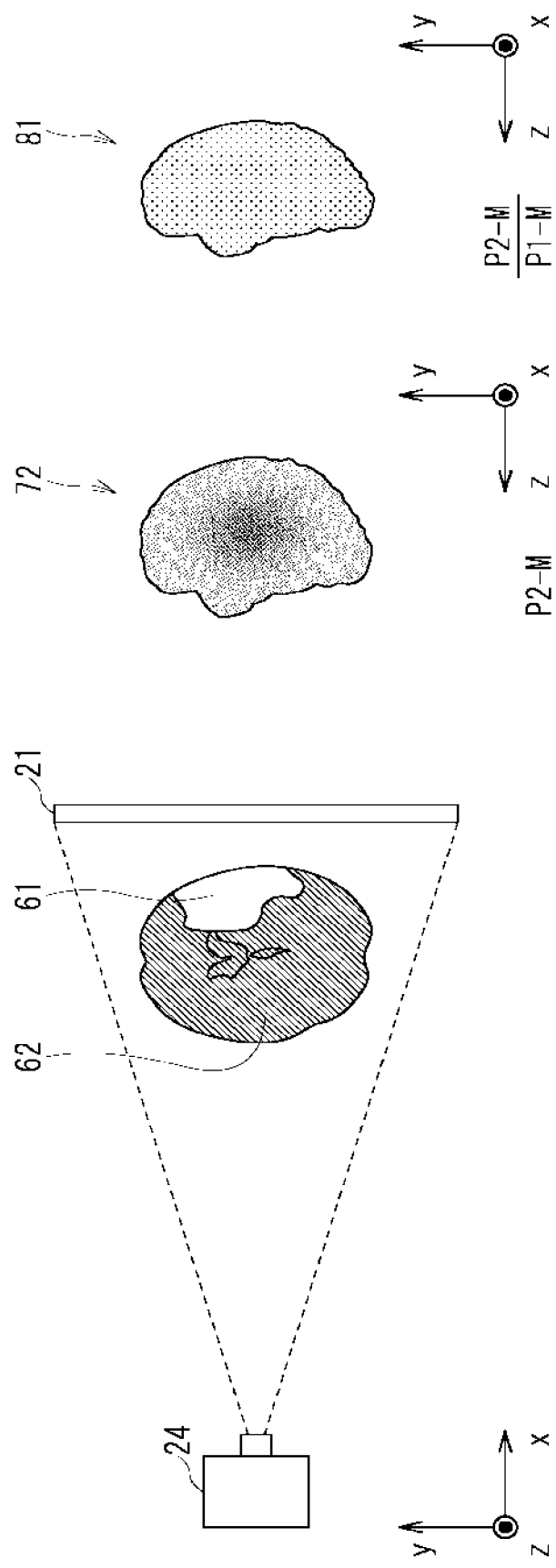

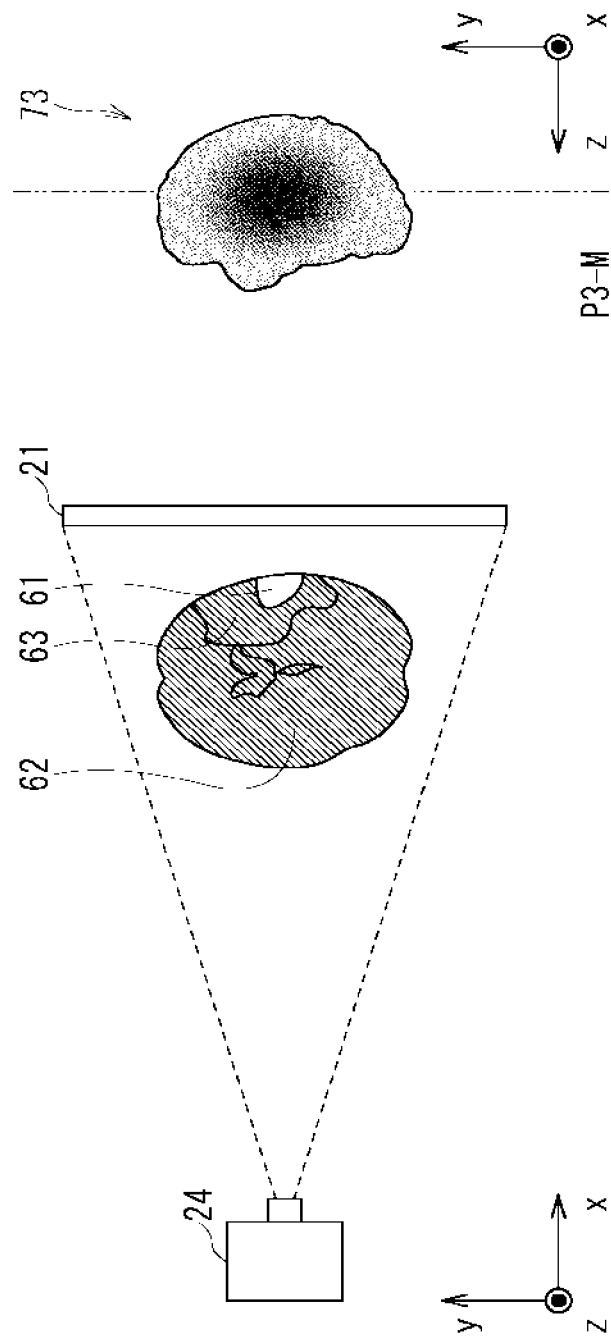

X-RAY DIAGNOSTIC APPARATUS, IMAGE PROCESSING APPARATUS, AND IMAGE PROCESSING METHOD

CROSS-REFERENCE TO RELATED APPLICATIONS

This application is a divisional application of U.S. application Ser. No. 15/048,289, filed Feb. 19, 2016, and claims the benefit of priority of Japanese Patent Application No. 2015-030133, filed Feb. 19, 2015, and claims the benefit of priority of Japanese Patent Application No. 2016-028954, filed Feb. 18, 2016. The entire contents of the above-identified applications are incorporated herein by reference.

FIELD

Embodiments described herein relate generally to an X-ray diagnostic apparatus, an image processing apparatus, and an image processing method.

BACKGROUND

Tests using an X-ray diagnostic apparatus include X-ray subtraction angiography. In this test, the same site of an object is taken as an image before contrast medium injection (mask image) and an image after contrast medium injection (contrast image). An image (subtraction image) obtained by calculating the difference between these images is generated.

The subtraction image is an image in which image portions of blood vessels are visualized with a contrast medium. A user can easily grasp the situation of bloodstreams in the object by observing the subtraction image. For example, in the case of thrombectomy using a catheter, it is expected to allow identification of whether bloodstreams are recovered or not in a territory of a thrombus by observing whether image portions of blood vessels downstream of a thrombus (i.e. vascular territory of the thrombus, hereinafter referred to as "territory") appears or not in the subtraction image after thrombectomy.

For example, in thrombectomy using a catheter for a patient of cerebral infarction, an operation of removing a thrombus is tried pharmacologically by a thrombolytic agent released from the distal end of the catheter or mechanically by a device protruding from the distal end of the catheter. In this case, it is preferred that each time the operation of removing a thrombus is performed, a user as a practitioner identifies whether the bloodstream in the territory is recovered or not. This identification method may be, for example, a method of consecutively taking X-ray images while releasing the contrast medium from the distal end of the catheter into a blood vessel, obtaining subtraction images, and observing whether an image portion of the blood vessel visualized in these subtraction image appears in the territory or not.

Unfortunately, according to this method, it is difficult to determine whether the bloodstream is restored across the entire territory on the basis of the subtraction images. The difficulty is because the contrast medium released from the distal end of the catheter circulates in a bloodstream to leave normal brain tissue to be also visualized and the visualized image portion is included in the subtraction images.

The present invention has an object to provide an X-ray diagnostic apparatus, an image processing apparatus, and an image processing method capable of generating the image that allows easy identification of bloodstream recovery in the territory, i.e. in the region including blood vessels downstream of a thrombus, during or after thrombectomy using the catheter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4A is a diagram illustrating an example of the situation of taking the first contrast image P1 of the head of the object P;

FIG. 4B is a diagram illustrating an example of the subtraction image as a first difference image (P1−M), which can be obtained using the first contrast image P1 and the mask image M;

FIG. 5A is a diagram illustrating an example of the situation of taking another first contrast image P2 of the head of the object P;

FIG. 5B is a diagram illustrating an example of the subtraction image as another first difference image (P2−M), which can be obtained using the other first contrast image P2 and the mask image M;

FIG. 5C is a diagram illustrating an example of an image as a ratio image 81 ((P2−M)/(P1−M)) having pixel values that are the ratios of pixel values between the other first difference image (P2−M) and the first difference image (P1−M);

FIG. 6A is a diagram illustrating an example of the situation of taking a second contrast image P3 of the head of the object P;

FIG. 6B is a diagram illustrating an example of a second difference image (P3−M), which can be obtained using the second contrast image P3 and the mask image M;

DETAILED DESCRIPTION

Hereinbelow, a description will be given of an X-ray diagnostic apparatus, an image processing apparatus, and an image processing method according to embodiments of the present invention with reference to the drawings.

In general, according to one embodiment, the X-ray diagnostic apparatus generating an X-ray image in a region of interest includes a radiography device and processing circuitry. The radiography device takes a first X-ray image before injection of a contrast medium, and takes a second X-ray image and a third X-ray image after injection of the contrast medium. The processing circuitry generates an output image having pixel values that are ratios of pixel values between a difference between the second X-ray image and the first X-ray image and a difference between the third X-ray image and the first X-ray image.

First Embodiment

Figure 1:
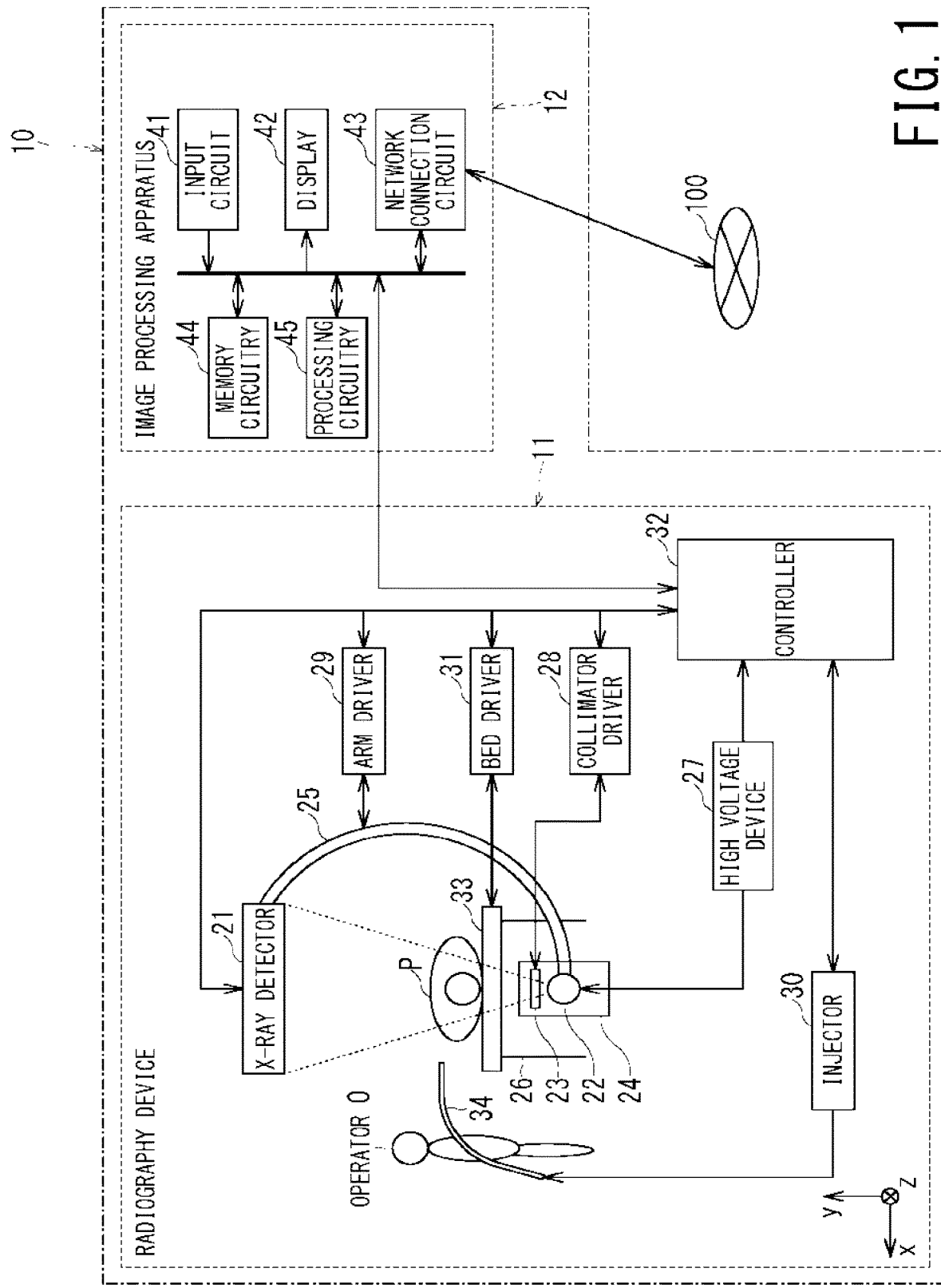
FIG. 1 is a block diagram showing an example of an X-ray diagnostic apparatus according to a first embodiment of the present invention.

FIG. 1 is a block diagram showing an example of an X-ray diagnostic apparatus 10 according to a first embodiment of the present invention.

As shown in FIG. 1, the X-ray diagnostic apparatus 10 includes a radiography device 11, and an image processing apparatus 12. The radiography device 11 of the X-ray diagnostic apparatus 10 is typically installed in a laboratory, and generates X-ray projection data pertaining to a site (a region of interest) of a patient P. The image processing apparatus 12, which is often installed in an operation room adjoining the laboratory, generates X-ray images based on the projection data, and displays the images.

The radiography device 11 includes: an X-ray detector 21; an X-ray generator 24 including an X-ray tube 22, and a collimator 23 for the X-ray tube 22; a C-arm 25; a bed 26; a high voltage device 27; a collimator driver 28; an arm driver 29; an injector 30; a bed driver 31; and a controller 32. The components 21 to 32 of the radiography device 11 may be conventionally known components.

The X-ray detector 21 is provided at one end of the C-arm 25 opposite to the X-ray tube 22 so as to sandwich the patient P supported on a tabletop (catheter table) 33 of the bed 26. The X-ray detector 21, which is made of a flat panel detector (FPD), detects X-rays with which the X-ray detector 21 is irradiated, and outputs X-ray projection data on the basis of the detected X-rays. The projection data is supplied to the image processing apparatus 12 through the controller 32. The X-ray detector 21 may include an image intensifier, a TV camera or the like.

The X-ray generator 24 is provided at the other end of the C-arm 25, and includes the X-ray tube 22 and the collimator 23.

The X-ray tube 22 is applied with voltage by the high voltage device 27, and generates X-rays. The X-rays generated by the X-ray tube 22 are emitted toward the object P.

The collimator 23 may be, for example, an X-ray irradiation field stop made of multiple lead blades. The collimator 23 is controlled by the controller 32 through the collimator driver 28, and adjusts the X-ray irradiation range irradiated with X-rays emitted from the X-ray tube 22.

The C-arm 25 holds the X-ray generator 24 and the X-ray detector 21 in an integrated manner. The C-arm 25 is controlled and driven by the controller 32, thereby allowing the X-ray generator 24 and the X-ray detector 21 to integrally move around the object P.

The bed 26 is installed on a floor, and holds the tabletop 33. The bed 26 is controlled by the controller 32, and moves and turns (rolls) the tabletop 33 in the horizontal direction and the vertical direction.

The high voltage device 27 is controlled by the controller 32, and supplies the X-ray tube 22 with power required for X-ray irradiation.

The collimator driver 28 is controlled by the controller 32 and adjusts the aperture of the collimator 23, which in turn adjusts the range irradiated with X-rays emitted from the X-ray tube 22 according to an imaging protocol.

The arm driver 29 and the bed driver 31 are controlled by the controller 32, and drive the C-arm 25 and the tabletop 33, respectively.

The injector 30 is a device that is controlled by the controller 32 and injects a contrast medium through the catheter 34 held by an operator O and inserted into an affected area of the object P. Timing of injecting the contrast medium and stopping the injection, and the concentration and injection speed of the contrast medium are automatically controlled by the controller 32. The injector 30 may be prepared as an external and isolated device different from the X-ray diagnostic apparatus 10. In this case, the X-ray diagnostic apparatus 10 does not include the injector 30. The injector 30 is not necessarily controlled by the controller 32 irrespective of whether the injector is prepared at the outside or not. For example, an instruction by the operator O may be accepted through an input section provided at the injector 30, and the contrast medium may be injected at the concentration, speed and timing according to the instruction.

The controller 32 is controlled by the image processing apparatus 12, and in turn controls the X-ray detector 21, the high voltage device 27, the collimator driver 28, the arm driver 29, the injector 30, and the bed driver 31, thereby taking X-ray images, generating projection data on the region of interest in the object P, and supplying the data to the image processing apparatus 12.

On the other hand, as illustrated in FIG. 1, the image processing apparatus 12 includes an input circuit 41, a display 42, a network connection circuit 43, memory circuitry 44, and processing circuitry 45. The components 41 to 45 of the image processing apparatus 12 may be made up of, for example, an information processing device, such as a typical personal computer or workstation.

The input circuit 41 includes, for example, a typical input device, such as a mouse, trackball, keyboard, touch panel, or numeric keypad, and a hand switch for instructing X-ray irradiation timing, and outputs, to the processing circuitry 45, an operational input signal corresponding to an operation by the user. A microphone for audio input may be adopted as the input circuit 41. In this case, the microphone converts a voice input by the user into a digital audio signal. The processing circuitry 45 applies an audio recognition process to the digital audio signal, thereby performing an operation according to the voice input by the user. The user may be identical to or different from the operator O.

The display 42, which may be, for example, a typical display output device, such as a liquid crystal display or OLED (Organic Light Emitting Diode) display, displays various images, such as X-ray images, according to the control by the processing circuitry 45.

The network connection circuit 43 is embedded with various information communication protocols in conformity with the geometry of a network 100. The network connection circuit 43 connects the X-ray diagnostic apparatus 10 to another apparatus according to the various protocols. Here, the network 100 means an information communication network using telecommunication techniques, and includes not only a wireless/wired LAN (Local Area Network), such as a hospital main LAN, and the Internet, but also a telephone communication network, an optical fiber communication network, a cable communication network, and a satellite communication network. In this embodiment, X-ray diagnostic apparatus 10 does not necessarily include the network connection circuit 43.

The memory circuitry 44 has a configuration including memory circuitry readable and writable by a processor of the processing circuitry 45, such as a magnetic or optical recording medium or a semiconductor memory, and is controlled by the processing circuitry 45 to store a mask image M and the positions and the like of the X-ray tube 22 and the X-ray detector 21 at the time of taking the mask image M with reference to the tabletop 33.

The processing circuitry 45 includes at least the processor. The processing circuitry 45 comprises, for example, the processor, RAM, and memory circuitry including ROM. The processing circuitry 45 controls the operation of X-ray diagnostic apparatus 10, which includes the controller 32, according to a program stored in the memory circuitry. The processor of the processing circuitry 45 loads, onto the RAM, an image processing program, and data required to execute the program stored in the memory circuitry typified by a ROM. The configuration illustrated in the description above may be what has been conventionally known.

The processor of the processing circuitry 45 of this embodiment executes a process for generating an image that allows easy confirmation of bloodstream recovery at an area downstream of a thrombus (territory) according to this image processing program, in thrombectomy using the catheter 34.

The RAM of the processing circuitry 45, which may be what have been conventionally used, provides a work area for temporarily storing programs executed by the processor, and data. The memory circuitry, typified by the ROM of the processing circuitry 45, stores a boot program and image processing program for X-ray diagnostic apparatus 10, and various data items for executing these programs.

The memory circuitry, which is typified by ROM and may be what has been conventionally used, has a configuration that includes memory circuitry readable by a processor, such as a magnetic or optical recording medium or a semiconductor memory. A part of or the entire programs and data in the memory circuitry may be configured to be downloadable via an electronic network. The processing circuitry 45 may be made up of multiple processors.

Figure 2:
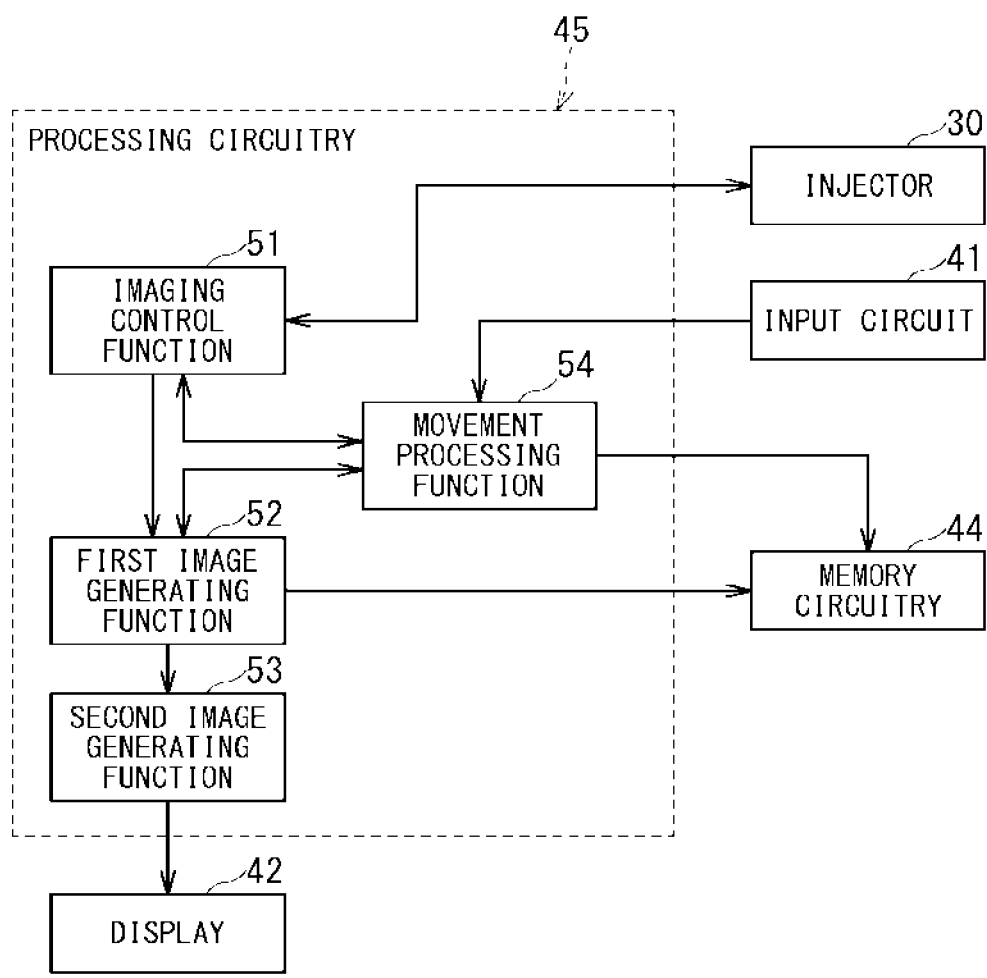
FIG. 2 is a schematic block diagram showing an example of functions achievable by the processor of the processing circuitry according to the first embodiment.

FIG. 2 is a schematic block diagram showing an example of functions achievable by the processor of the processing circuitry 45 according to the first embodiment.

As shown in FIG. 2, the processor of the processing circuitry 45 functions at least as an imaging control function 51, a first image generating function 52, a second image generating function 53, and a movement processing function 54, according to the image processing program. These functions are stored in the memory circuitry in forms of respective programs.

The imaging control function 51, which may be what has been conventionally used, takes X-ray images before and after injection of the contrast medium by controlling the radiography device 11 through the controller 32.

The first image generating function 52 generates a digital image having pixel values that are the logarithms of the intensity of X-rays having passed through the object P, on the basis of the projection data. For example, the first image generating function 52 generates a mask image on the basis of projection data obtained by X-ray imaging before an operation of removing a bloodstream obstruction, such as a plaque or thrombus, and before contrast medium injection. The first image generating function 52 generates a first contrast image on the basis of projection data obtained by X-ray imaging before the operation of removing the bloodstream obstruction and after contrast medium injection. The first image generating function 52 generates a second contrast image on the basis of projection data obtained by X-ray imaging after the operation of removing the bloodstream obstruction and after contrast medium injection.

Here, a conventional subtraction image is briefly described. The following description is for the case where the object P causes cerebral infarction, the bloodstream obstruction is a thrombus, the region of interest including the bloodstream obstruction is the head of the object P, and an operation of removing the bloodstream obstruction is thrombectomy using the catheter 34. The cerebral infarction is a pathological condition where a cerebral artery is clogged with a thrombus or the like, and no blood flows through tissue downstream of the artery (territory) or the flow rate of blood significantly decreases.

A first alternative of a method of treating a cerebral infarction patient is administration of a thrombolytic agent into a vein. There is a limitation where the administration has to be made within a limited time, which varies among areas in the world. The administration has a low success rate, which is a probability that the thrombus dissolves and the flow rate of blood is sufficiently recovered (restored).

For a case where a thrombolytic agent has been unable to be administered into a vein within a limited time, a case where the disease-onset time is unknown, or a case where the thrombolytic agent has been administered but has been unsuccessful, the thrombectomy using the catheter 34 is performed as a second alternative of the treatment method for a cerebral infarction patient.

The thrombectomy using the catheter 34 is an operation of inserting the catheter 34 into a cerebral blood vessel and removing a thrombus while consecutively taking X-ray images of the head of the object P (i.e., under X-ray fluoroscopy). In thrombectomy using the catheter 34, the operation of removing the thrombus is tried pharmacologically by the thrombolytic agent released from the distal end of the catheter 34 or mechanically by a device protruding from the distal end of the catheter 34.

In the case of using the thrombolytic agent, the thrombolytic agent is released from the distal end of the catheter 34 and the area is left as it is awhile.

In the case of mechanically removing the thrombus, a device for wrapping the thrombus is caused to protrude from the distal end of the catheter 34, the contrast medium is released while X-ray images of the head of the object P are consecutively taken, the position of the thrombus is identified, the device is inserted into the thrombus to wrap the thrombus with the device. Next, the device is extracted, thereby removing many parts of the thrombus.

According to another method of mechanically removing a thrombus, a device for crushing the thrombus is caused to protrude from the distal end of the catheter 34, the contrast medium is released while images of the head of the object P are consecutively taken, and the position of the thrombus is identified, the device is inserted into the thrombus. The device outputs ultrasonic waves or the like to crush the thrombus. The crushed fragments are sucked out through the catheter.

In the case of thrombectomy using the catheter 34, it is important that each time the operation of removing a thrombus is performed, a user as a practitioner identifies whether the bloodstream in the territory is recovered or not. It is thus preferred that X-ray images of the head of the object P be consecutively taken while the contrast medium be being released in the artery from the distal end of the catheter 34, and observation be made on whether a visualized vascular image appear in the territory or not. When the thrombus is sufficiently removed, images of arterial branches, capillary-vascular networks, and veins in the territory appear.

The arterial branches or the capillary-vascular network in the territory may sometimes be clogged with another thrombus. In some cases, this pathological condition may have originally occurred. In other cases, this condition may be caused because the debris of the thrombus has been caused by the thrombectomy, flown downstream, and caused clogging. In these cases, only parts of the arterial branches and the capillary-vascular networks in the territory are imaged.

For generating images for observing such types of bloodstream situations, it has been known that generation of a subtraction image (difference image) is effective in removing image portions caused by the contrast medium having been dispersed in tissue, such as of the skull, or in blood.

To generate the difference image, first, the first image generating function 52 generates a mask image M on the basis of projection data obtained by X-ray imaging before the operation of removing a thrombus and before contrast medium injection. The image is generated before the operation of removing the thrombus, and it can thus be considered that a region 61 with no bloodstream in the cerebral artery coincides with the territory.

Figure 3:
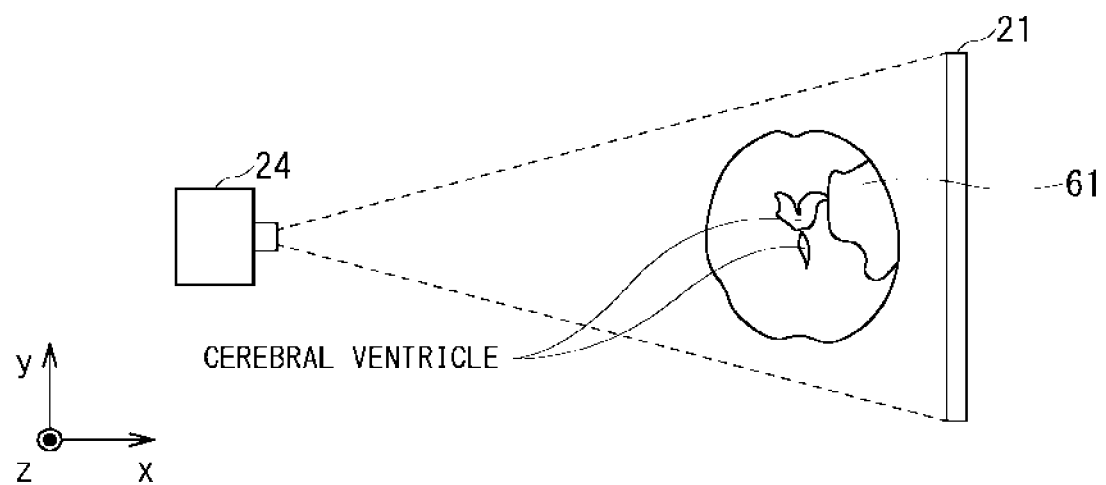
FIG. 3 is a diagram illustrating an example of the situation of taking the mask image M of the head of the object P.

FIG. 3 is a diagram illustrating an example of the situation of taking the mask image M of the head of the object P. FIG. 4A is a diagram illustrating an example of the situation of taking the first contrast image P1 of the head of the object P. FIG. 4B is a diagram illustrating an example of the subtraction image (first difference image) 71 (P1−M), which can be obtained using the first contrast image P1 and the mask image M.

When the contrast medium is injected before the operation of removing the thrombus, the region 62 upstream of the territory is stained with the contrast medium (see the hatched region in FIG. 4A). For example, the first image generating function 52 generates the first contrast image P1 on the basis of the projection data obtained by taking X-ray images while releasing the contrast medium from the distal end of the catheter 34 into the artery. Preferably, the first contrast image P1 is generated on the basis of the projection data obtained by taking X-ray images after a lapse of time during which the contrast medium is uniformly distributed across tissue after administration of the contrast medium.

The second image generating function 53 generates the first difference image 71 (P1−M) with pixel values that are the differences between the pixel values of the pixels of the first contrast image P1 and the pixel values of the pixels of the mask image M (see FIG. 4B).

As shown in FIG. 4B, the pixels corresponding to the territory in the first difference image 71 (P1−M) do not have uniform pixel values. This nonuniformity is because the X-ray transparent length for the contrast medium having dispersed in the object P varies according to the positions of the pixels.

For example, when the contrast medium is injected through the catheter in the artery, the blood vessel, the blood vessel branches downstream of the vessel, capillary-vascular networks in the territory downstream of the branches, and the veins downstream of the networks are visualized. At this time, the capillary-vascular networks are very fine and the number of networks is significantly large. Consequently, the networks cannot be individually viewed but appear as if they were cloud. When the capillary-vascular networks in the territory are uniformly visualized, the pixels corresponding to the first difference image 71 (P1−M) in the territory have uniform pixel values according to use of images taken by the X-ray CT apparatus. However, as to images taken by the X-ray diagnostic apparatus 10, the X-ray transparent length for the contrast medium dispersing over the object P varies with the pixel positions. Consequently, the attenuating effect due to the contrast medium varies with the pixel positions. Thus, even if the capillary-vascular networks in the territory are uniformly visualized, the portions corresponding to the territory of the first difference image 71 (P1−M) generated by the X-ray diagnostic apparatus 10 are not uniform (see FIG. 4B).

FIG. 5A is a diagram illustrating an example of the situation of taking another first contrast image P2 of the head of the object P. FIG. 5B is a diagram illustrating an example of the subtraction image (another first difference image) 72 (P2−M), which can be obtained using the other first contrast image P2 and the mask image M. FIG. 5C is a diagram illustrating an example of an image (hereinafter, referred to as a ratio image) 81 ((P2−M)/(P1−M)) having pixel values that are the ratios of pixel values between the other first difference image 72 (P2−M) and the first difference image 71 (P1−M).

For example, the contrast medium for taking the first contrast image P1 is dispersed in the blood. Consequently, when the first contrast image P2 is taken again, this image is thus taken in the state with an increased contrast medium concentration (the amount of contrast medium contained in living tissue having a unit volume) that is higher than that for P1. In this case, as with the first difference image 71 (P1−M), the other first difference image 72 (P2−M) have pixels corresponding to the territory that do not have uniform pixel values (see FIG. 5B).

Thus, even if there is a region where restoration of the bloodstream (the clogging of the blood vessel is removed, and the flow rate of blood is sufficiently recovered) due to thrombectomy increases the contrast medium concentration (the amount of contrast medium contained in the living tissue having a unit volume), it is difficult to identify the region due to nonuniformity of the pixel values of the portions corresponding to the territory through the difference images 71 and 72. It is thus difficult to determine whether the thrombectomy has succeeded or not. Even if the difference image ((P1−M)−(P2−M))=(P1−P2) between the first difference image 71 (P1−M) and the other first difference image 72 (P2−M) is generated, each of the pixels of the portions corresponding to the territory in the difference image (P1−P2) do not have unique pixel value because the contrast medium concentrations (the amount of contrast medium contained in living tissue having a unit volume) in the difference images 71 and 72 are different from each other.

The second image generating function 53 of the X-ray diagnostic apparatus 10 according to this embodiment generates a ratio image having pixel values that are the ratios of pixel values between the difference images. The ratio image generated from between the difference images is an image in which the ratios of the contrast medium concentration (the amount of contrast medium in living tissue having a unit volume) at the time of imaging in the contrast images of the difference images are reflected. Consequently, the pixels of the portions corresponding to the territory in the ratio image have substantially uniform pixel values.

For example, as shown in FIG. 5C, the ratio image 81 ((P2−M)/(P1−M)) having pixel values that are the ratios of the pixel values of the pixels of the other first difference image 72 (P2−M) and the pixel values of the pixels of the first difference image 71 (P1−M) is an image in which only increase in contrast medium concentration (the amount of contrast medium contained in living tissue having a unit volume) is reflected, and is an image having a uniform portion corresponding to the territory (see FIG. 5C).

FIG. 6A is a diagram illustrating an example of the situation of taking a second contrast image P3 of the head of the object P. FIG. 6B is a diagram illustrating an example of a second difference image 73 (P3−M), which can be obtained using the second contrast image P3 and the mask image M.

Figure 7:
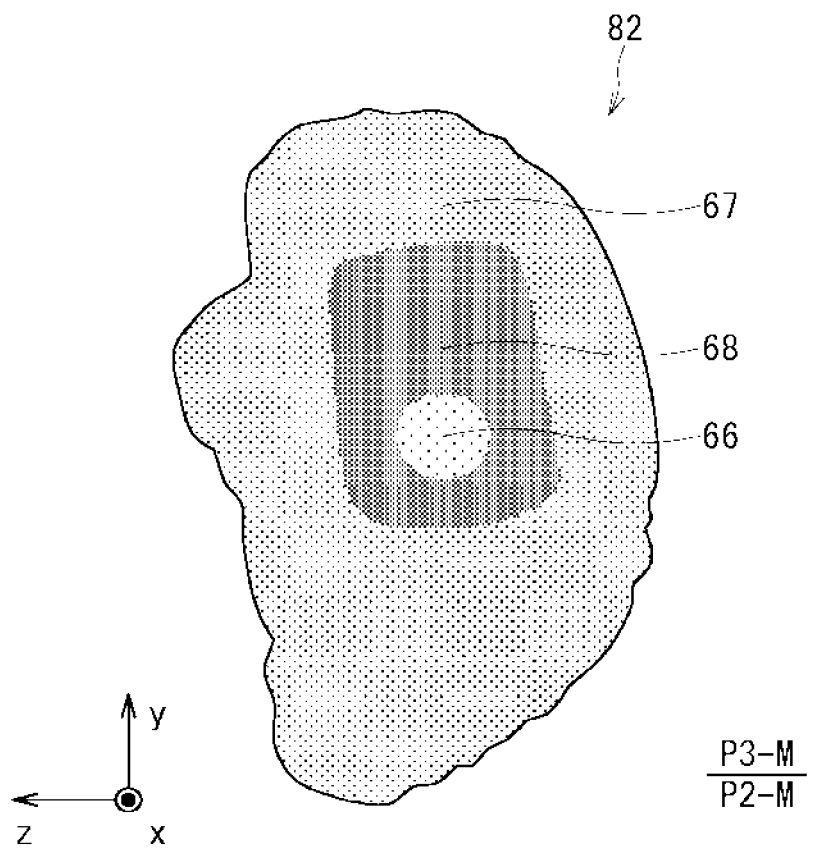
FIG. 7 is a diagram illustrating an example of a ratio image ((P3−M)/(P2−M)) having pixel values that are the ratios of pixel values between the second difference image (P3−M) and the other first difference image (P2−M)

FIG. 7 is a diagram illustrating an example of a ratio image 82 ((P3−M)/(P2−M)) having pixel values that are the ratios of pixel values between the second difference image 73 (P3−M) and the other first difference image 72 (P2−M). An image portion 66 in FIG. 7 is an example of an image portion caused by X-rays having passed through a region 63, a region 62 and a region 61 (see FIG. 6A). In FIG. 7, the image portion 67 is an example of an image portion generated by X-rays having passed through only the region 63, while the image portion 68 is an example of an image portion generated by X-rays having passed through the regions 63 and 62. Alternatively, instead of the other first difference image 72 (P2−M) in FIGS. 6B and 7, the first difference image 71 (P1−M) may be used.

The case is considered where the operation of removing a thrombus allows a bloodstream recovered at a part of the territory. In this case, when the contrast medium is injected after the operation of removing the thrombus, the region 63 in FIG. 6A where the bloodstream is recovered is stained with the contrast medium but no contrast medium enters the region 61 in FIG. 6A where the bloodstream is not recovered.

At this time, first, the second image generating function 53 generates the second difference image 73 (P3−M) with pixel values that are the differences between the pixel values of the pixels of the second contrast image P3 and the pixel values of the pixels of the mask image M (see FIG. 4B). However, as with the other first difference image 72 (P2−M) and the first difference image 71 (P1−M), the second difference image 73 (P3−M) is an image with the pixels of a portion corresponding to the territory that have nonuniform pixel values (see FIG. 6B).

Subsequently, the second image generating function 53 generates a ratio image 82 ((P3−M)/(P2−M) (or (P3−M)/(P1−M))) having pixel values that are the ratios between the pixel values of pixels of the second difference image 73 (P3−M) and the pixel values of pixels of the other first difference image 72 (P2−M) (or a first difference image 71 (P1−M)).

The second difference image 73 (P3−M) shown in FIG. 6B is an image with pixels of the portion corresponding to the territory that are nonuniform. Consequently, even if the region 63 with the contrast medium concentration (the amount of contrast medium contained in living tissue having a unit volume) being high due to recovery of the bloodstream exists, it is difficult to determine the region 63 owing to adverse effects of nonuniformity of pixel values of pixels of the portion corresponding to the territory only by comparison between FIGS. 6B and 5B.

On the other hand, as shown in FIG. 7, according to the ratio image 82, there is no increase in bloodstream between the second difference image 73 (P3−M) and the other first difference image 72 (P2−M) at the image portion 67 generated by X-rays having passed through the region 62 in FIG. 6A which is corresponding to upstream of the thrombus, but only the contrast medium concentration (the amount of contrast medium contained in living tissue having a unit volume) varies. Consequently, the image portion 67 has a substantially identical pixel value "a" over the entire region. Meanwhile, the pixels corresponding to the image portion 68 generated by X-rays having passed through the region 63 in FIG. 6A where the bloodstream is recovered have pixel values in which increase in contrast medium concentration due to increase in bloodstream is reflected in the second difference image 73 (P3−M), in comparison with the other first difference image 72 (P2−M). Consequently, the pixels of the image portion 68 have a pixel value "b", which is different from that of the pixels of the image portion 67.

The ratio between the pixel value "a" and the pixel value "b" is approximately proportional to the magnitude obtained by multiplying the thickness of the portion where the bloodstream is recovered by the amount of contrast medium in the blood contained in the portion. For example, if the territory covers approximately half of the brain, recovery across the entire territory causes the pixel value "b" to be approximately twice as high as the pixel value "a".

Thus, the ratio image 82 becomes an image representing a region where the bloodstream is recovered by thrombectomy performed between taking the first contrast image P1 or the other first contrast image P2 and taking the second contrast image P3. Consequently, the user can easily and securely grasp the bloodstream restored region by observing the ratio image 82. An image of the territory obtained by another modality, such as an X-ray CT (Computed Tomography) apparatus or a magnetic resonance imaging (MRI) apparatus is compared with the ratio image 82 and observed, thereby allowing the user to obtain information on the restored region in more detail.

The mask image M, the first contrast images P1 and P2, and the second contrast image P3 are computed assuming that each pixel value reflects the X-ray fluorescence intensity at the same position. Consequently, it is preferred that the images be from the same viewpoint.

The movement processing function 54 causes the memory circuitry 44 to store the positions of the X-ray tube 22 and the X-ray detector 21 with reference to the tabletop 33 at the time of taking the mask image M, and this mask image M. The movement processing function 54 moves the X-ray tube 22 and the X-ray detector 21 to the positions stored in the memory circuitry 44 at the time of taking the first contrast images P1 and P2, and the second contrast image P3 such that the first contrast images P1 and P2, and the second contrast image P3 should be from the same viewpoint.

For reducing the adverse effects and the like due to the body motion of the object P, the movement processing function 54 finely adjusts the positions of the X-ray tube 22 and the X-ray detector 21 through a process of matching the X-ray fluoroscopic image with an the mask image M at the positions after movement such that the X-ray fluoroscopic image should be from the same viewpoint as that of the mask image M. Various types of matching processes have been conventionally known in the technical field of image processing. Any of the types may be adopted. The imaging control function 51 then takes the first contrast images P1 and P2, and the second contrast image P3 after the fine adjustment. The movement processing function 54 allows the first contrast images P1 and P2 and the second contrast image P3, and the mask image M to be configured from the same viewpoint.

The movement processing function 54 may cause the memory circuitry 44 to store the positions of the X-ray tube 22 and the X-ray detector 21 with reference to the tabletop 33 and the mask image M at the time of taking the mask image M according to an instruction for "storing" issued by the user through the input circuit 41. When an instruction for "reproduction" is issued by the user through the input circuit 41 at the time of taking the first contrast images P1 and P2, and the second contrast image P3, the positions of the X-ray tube 22 and the X-ray detector 21 may be adjusted such that the first contrast images P1 and P2 and the second contrast image P3 may be configured to be from the same viewpoint as that of the mask image M according to the instruction.

Next, an example of the operation of the X-ray diagnostic apparatus 10 according to this embodiment is described.

Figure 8:
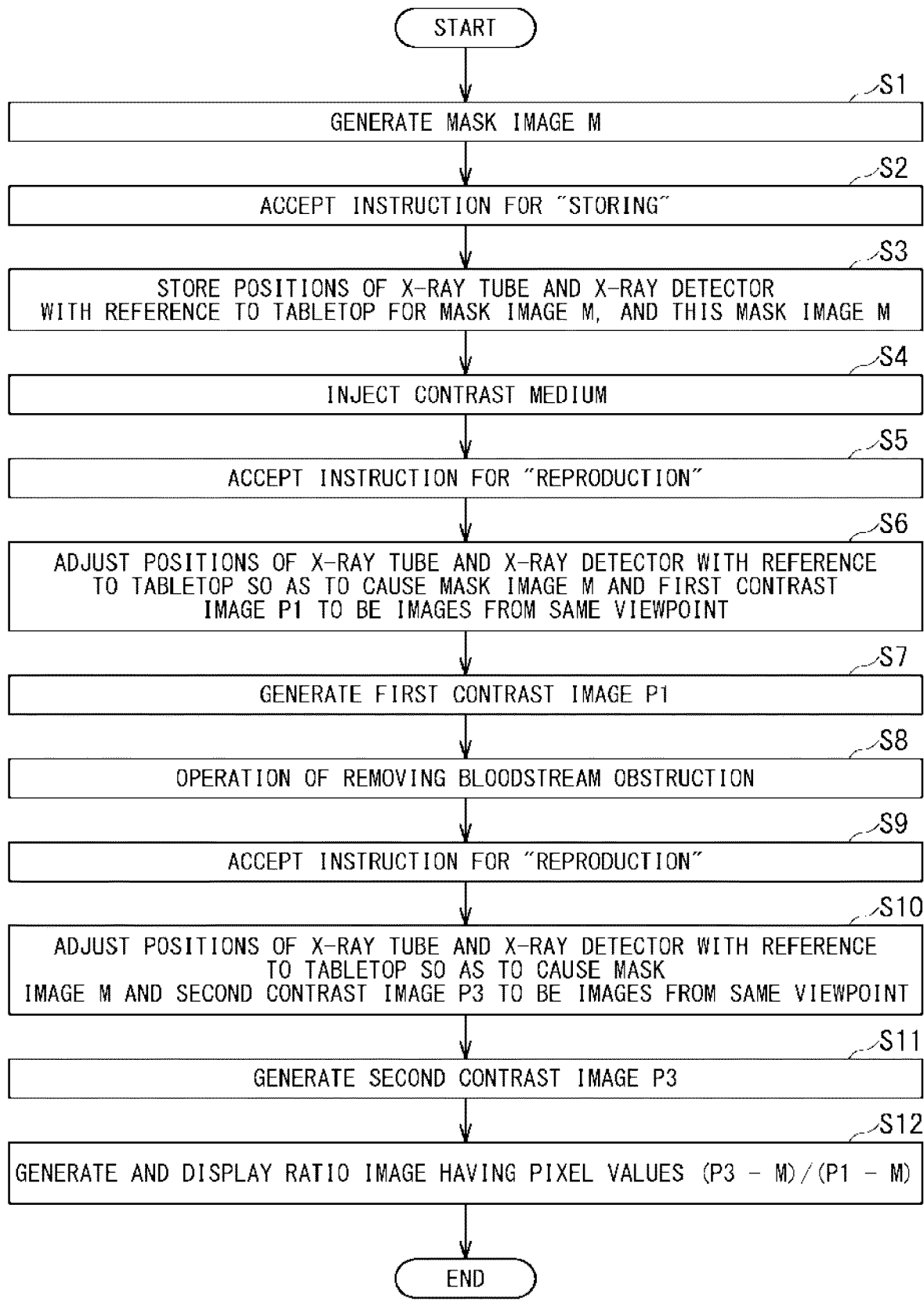
FIG. 8 is a flowchart showing an example of procedures of causing the CPU of the processing circuitry shown in FIG. 1 to generate an image that allows easy identification of bloodstream recovery downstream (territory) of a thrombus in thrombectomy using the catheter.

FIG. 8 is a flowchart showing an example of procedures of causing the CPU of the processing circuitry 45 shown in FIG. 1 to generate an image that allows easy identification of bloodstream recovery downstream of a thrombus (territory) in thrombectomy using the catheter 34. In FIG. 8, each step of the flowchart is represented by a symbol S assigned a numeral.

First, in step S1, the first image generating function 52 generates the mask image M. Next, in step S2, the movement processing function 54 accepts the instruction for "storing" from the user through the input circuit 41. Steps S1 and S2 may be simultaneously performed in parallel. Alternatively the order may be inverted.

Next, in step S3, the movement processing function 54 causes the memory circuitry 44 to store the mask image M and the positions of the X-ray tube 22 and the X-ray detector 21 with reference to the tabletop 33 at the time of taking the mask image M.

Next, in step S4, the imaging control function 51 injects the contrast medium into the object P through the injector 30. Next, in step S5, the movement processing function 54 accepts the instruction for "reproduction" from the user through the input circuit 41. Steps S4 and S5 may be simultaneously performed in parallel. Alternatively, the order may be inverted.

Next, in step S6, the movement processing function 54 adjusts the positions of the X-ray tube 22 and the X-ray detector 21 with reference to the tabletop 33 so as to cause the images from the same viewpoint as that of the mask image M to be generated.

Next, in step S7, the first image generating function 52 generates the first contrast image P1.

Next, in step S8, the operator O performs an operation of removing a bloodstream obstruction using the catheter 34.

Next, in step S9, the movement processing function 54 accepts the instruction for "reproduction" from the user through the input circuit 41.

Upon receipt of this instruction, in step S10, the movement processing function 54 adjusts the positions of the X-ray tube 22 and the X-ray detector 21 with reference to the tabletop 33 so as to cause the images from the same viewpoint as that of the mask image M to be generated.

Next, in step S11, the imaging control function 51 injects the contrast medium into the object P through the injector 30. The first image generating function 52 then generates the second contrast image P3.

Next, in step S12, the second image generating function 53 generates a ratio image 82 ((P3−M)/(P1−M) (or (P3−M)/(P2−M))) having pixel values that are the ratios between the pixel values of pixels of the second difference image 73 (P3−M) and the pixel values of pixels of the first difference image 71 (P1−M) (or the other first difference image 72 (P2−M)), and displays the generated image on the display 42 (see FIG. 7).

The above procedures can generate the ratio image 82 that allows easy identification of bloodstream recovery downstream of the thrombus (territory), and display this image during or after thrombectomy using the catheter 34.

The X-ray diagnostic apparatus 10 including the image processing apparatus 12 according to this embodiment can thus generate the ratio image 82. According to the ratio image 82, there is no increase in bloodstream at the image portion 67 generated by X-rays having passed only through the region 62 upstream of the thrombus between the second difference image 73 (P3−M) and the first difference image 71 (P1−M), but only the contrast medium concentration (the amount of contrast medium contained in living tissue having a unit volume) varies. Consequently, the image portion 67 has a substantially identical pixel value "a" across the entire region. Meanwhile, at the image portion 68 generated by X-rays having passed through the region 63 where the bloodstream is recovered, the bloodstream has increased in the second difference image 73 (P3−M) in comparison with the first difference image 71 (P1−M). Consequently, the pixels of the image portion 68 have various pixel values "b" different from those of the image portion 67.

Consequently, the X-ray diagnostic apparatus 10 allows the user to easily and securely grasp the bloodstream restored region by observing the ratio image 82.

In general, thrombectomy using the catheter 34 requires repeatedly taking X-ray images while releasing the contrast medium from the catheter 34 for the sake of an operation of inserting and advancing the catheter 34 to a site of a thrombus and an operation of removing the thrombus.

The contrast medium is dissolved in the blood and circulates over the entire body, a part of the contrast medium in the blood is gradually filtered by kidneys and excreted. Consequently, the contrast medium concentration in the blood very slightly decreases. However, in the thrombectomy using the catheter 34, the contrast medium is frequently and repeatedly released. Consequently, the increase in contrast medium concentration in the blood far exceeds the amount of decrease due to filtration. Note that the contrast medium has a side effect of affecting the renal function. Consequently, even for patients having a normal renal function, the total amount of usable contrast medium is limited with an upper limit. In particular, for patients having a renal function disorder, a side effect of significantly worsening the renal function disorder is caused by the contrast medium.

Consequently, the upper limit of the usable contrast medium should be strictly restricted. In other words, the operator O is imposed to decide to select one between two ways. According to one way, the sufficient therapy for the cerebral infarction is abandoned, which causes disorders, such as in movement and sensation, even if the life can be saved, and in turn causes the necessity of long-term rehabilitation. According to the other way, the renal function disorder is worsened, which causes the necessity of persistent dialysis or renal transplantation.

In consideration of this point, according to the X-ray diagnostic apparatus 10 according to this embodiment, the user can significantly easily grasp whether the bloodstream is recovered in the territory or not through observation of the ratio image 82. Consequently, this apparatus can significantly reduce the amount of use of the contrast medium in comparison with the conventional technique that simply compares the first difference image 71 and the second difference image 73 with each other.

Second Embodiment

Next, a second embodiment of the present invention, an X-ray diagnostic apparatus, an image processing apparatus, and an image processing method according to the present invention are described.

Figure 9:
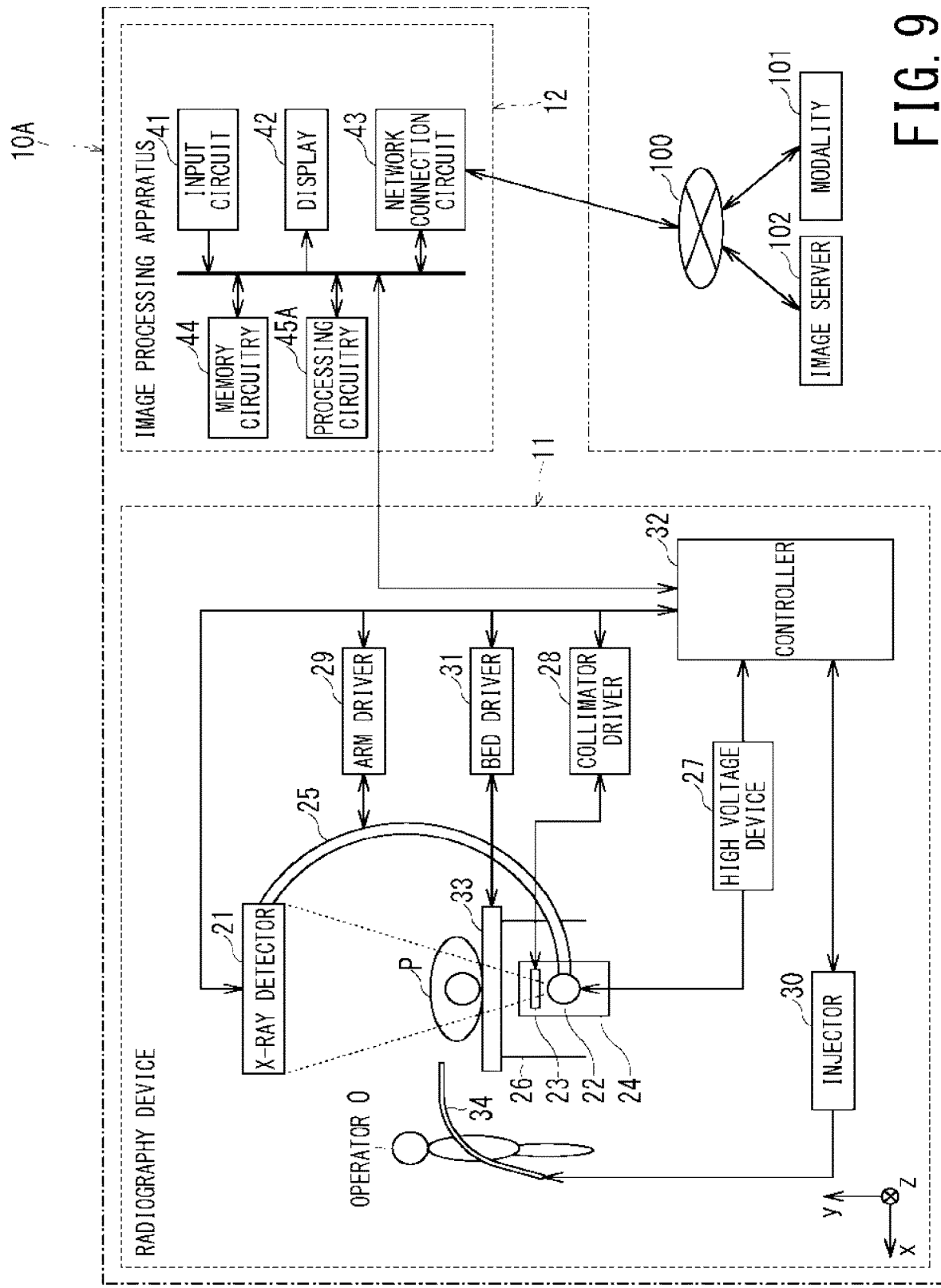
FIG. 9 is a block diagram showing an example of an X-ray diagnostic apparatus according to the second embodiment of the present invention.

FIG. 9 is a block diagram showing an example of an X-ray diagnostic apparatus 10A according to the second embodiment of the present invention.

The X-ray diagnostic apparatus 10A according to the second embodiment is different from the X-ray diagnostic apparatus 10 according to the first embodiment in that the apparatus 10A generates a predictive ratio image 90 of a ratio image 82 through simulation. The other configuration elements and operations are not different from those of the X-ray diagnostic apparatus 10 shown in FIG. 1 in a practical view. Consequently, the same configuration elements are assigned the same symbols. The description thereof is omitted.

The X-ray diagnostic apparatus 10A obtains volume data (medical three-dimensional image data) on the region of interest of the object P from a modality 101 or an image server 102 connected via the network 100, and causes the memory circuitry 44 to preliminarily store the data. A part of or the entire data stored in the memory circuitry 44 may be configured to be downloaded via the network 100, or stored through a portable memory medium, such as an optical disk.

The modality 101 is, for example, a medical image diagnostic apparatus, such as an X-ray CT (Computed Tomography) apparatus, an MRI (Magnetic Resonance Imaging) apparatus, an ultrasonic diagnostic apparatus, or an X-ray diagnostic apparatus, and may be any apparatus that can generate volume data (medical three-dimensional image data) on the basis of the projection data obtained through imaging of the object P (patient).

The image server 102 is, for example, a server that is provided for a PACS (Picture Archiving and Communication System) and is for long-term storage of images. This server stores a reconstructed image or volume data generated by the modality 101 connected via the network 100.

Figure 10:
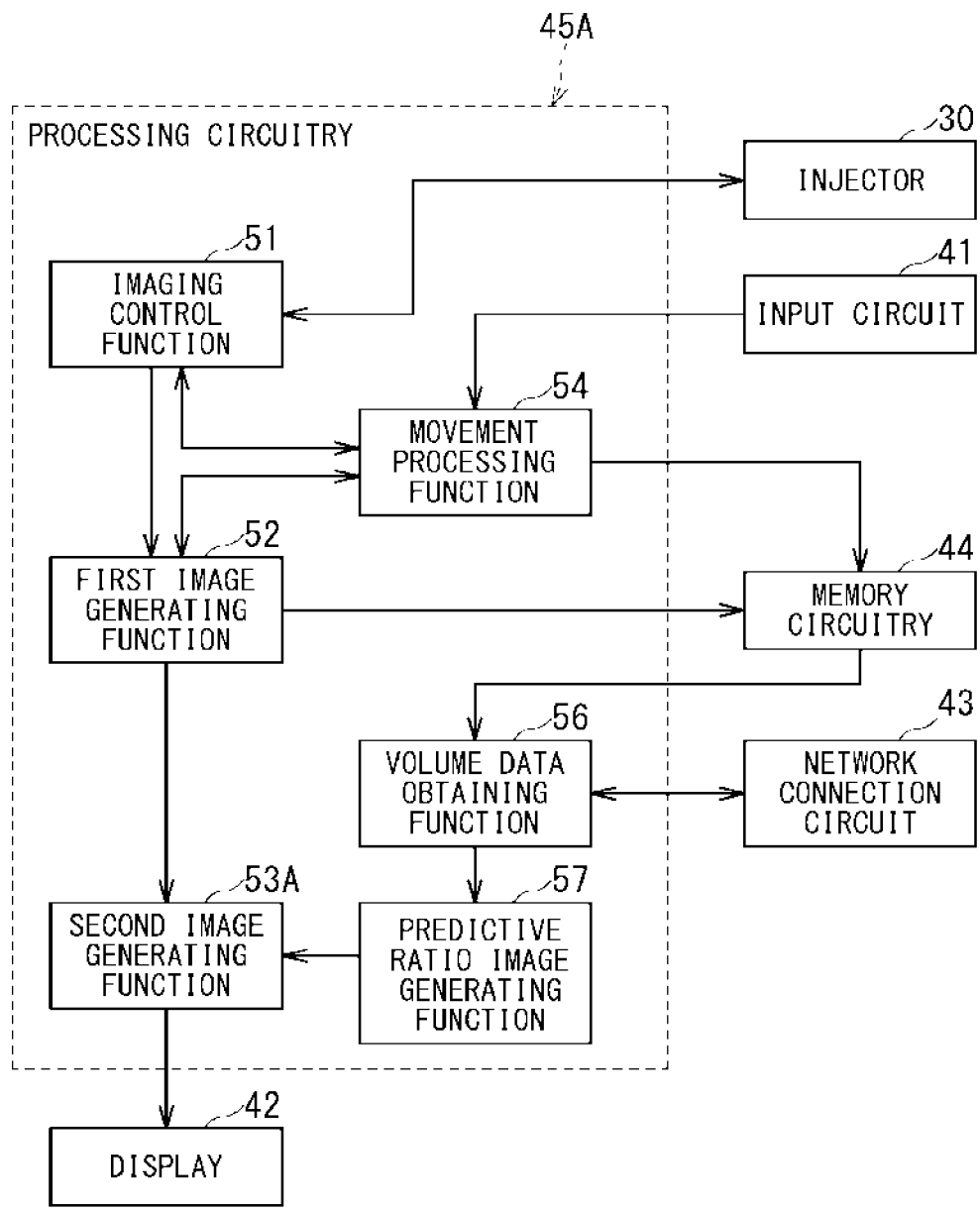
FIG. 10 is a schematic block diagram showing a configuration example of functions actualized by a CPU of the processing circuitry according to the second embodiment.

FIG. 10 is a schematic block diagram showing a configuration example of functions actualized by a CPU of the processing circuitry 45A according to the second embodiment. These achieved functions may be made up of hardware logics, such as circuits, instead of the CPU.

A volume data obtaining function 56 obtains volume data on the region of interest of the object P. The data is preliminarily stored in the memory circuitry 44, or obtained from the modality 101 or the image server 102 via the network connection circuit 43 and the network 100.

A predictive ratio image generating function 57 generates a predictive image of the first difference image 71 (predictive first difference image) through simulation using the volume data on the region of interest. The predictive ratio image generating function 57 generates a predictive image of the second difference image 73 (predictive second difference image) predicted to be obtained in the case where the bloodstream obstruction is completely removed, through simulation using the volume data on the region of interest.

Furthermore, the predictive ratio image generating function 57 generates a predictive ratio image 90 (E) having pixel values that are the ratios of pixel values between the predictive second difference image and the predictive first difference image.

Figure 11:
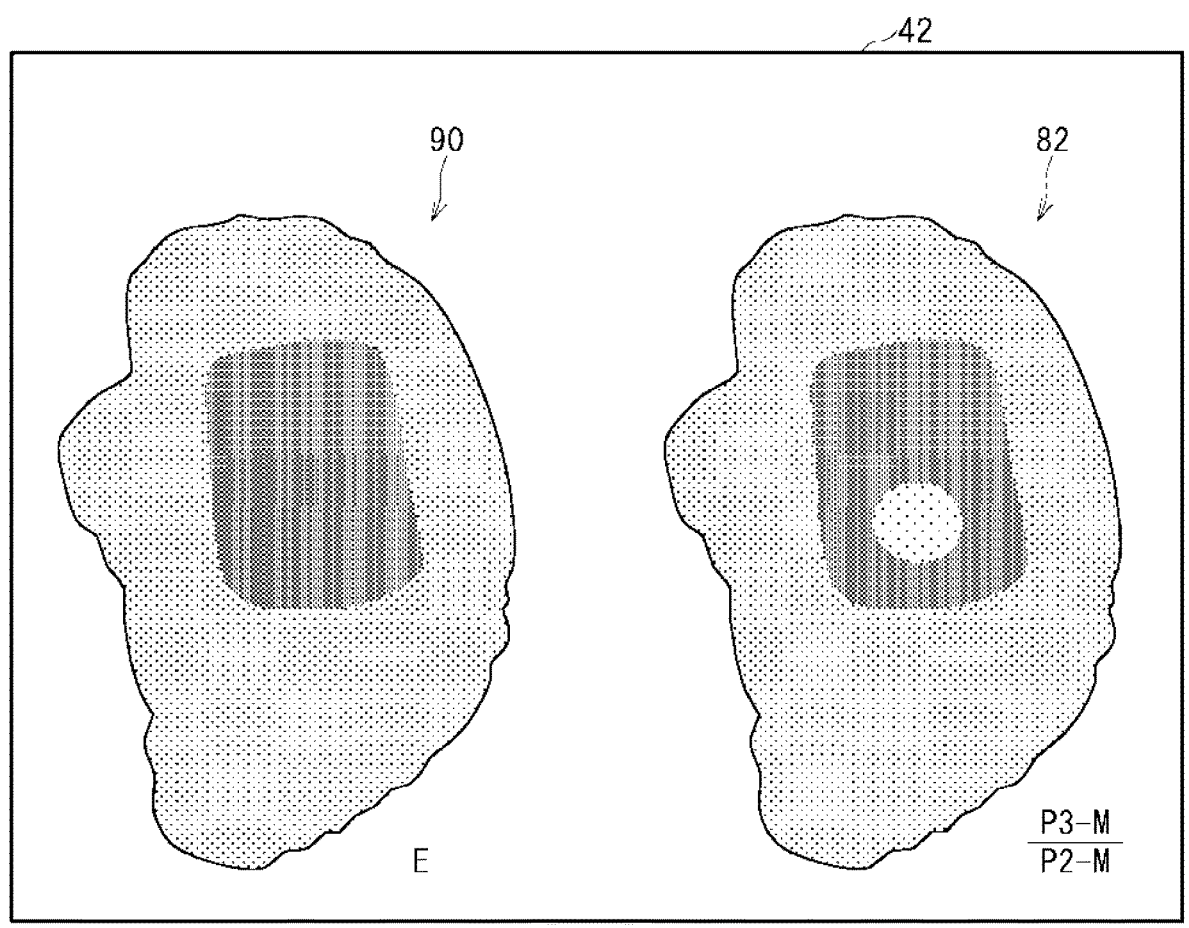
FIG. 11 is a diagram illustrating an example of a situation where the predictive ratio image (E) and the ratio image are displayed on the display in parallel.

FIG. 11 is a diagram illustrating an example of a situation where the predictive ratio image 90 (E) and the ratio image 82 are displayed on the display 42 in parallel.

The second image generating function 53A according to this embodiment displays the ratio image 82 generated on the basis of the projection data obtained by taking X-ray images of the region of interest of the object P (see FIG. 7), and the predictive ratio image 90 (E) generated by the predictive ratio image generating function 57, on the display 42 in parallel (see FIG. 11).

The predictive ratio image 90 (E) is the ratio image 82 predicted to be obtained in the case where the bloodstream obstruction is completely removed. Consequently, the user can easily identify the bloodstream restoration site and the degree of restoration by comparing and observing the ratio image 82 and the predictive ratio image 90 (E) with each other.

The second image generating function 53A may generate a comparison assistance image having pixel values that are the ratios of the pixel values of pixels of the predictive ratio image 90 (E) and the pixel values of pixels of the ratio image 82, and display the image on the display 42. The comparison assistance image is an image where only portions having not been restored are extracted. Consequently, the user can easily identify the bloodstream restoration site and the degree of restoration through observation of the comparison assistance image. It is the matter of course that the second image generating function 53A may display all the ratio image 82, the predictive ratio image 90 (E) and the comparison assistance image on the display 42 in parallel.

The simulation using the volume data by the predictive ratio image generating function 57 is herein described. Note that the predictive ratio image generating function 57 should generate the predictive first difference image and the predictive second difference image through calculation based on the volume data on the region of interest so as to configure the predictive ratio image 90 (E) to be configured from the same viewpoint as that of the ratio image 82.

First, the predictive ratio image generating function 57 extracts a focal portion of cerebral infarction by an appropriate image processing or a manual operation, from the volume data generated by the X-ray CT apparatus or the MRI apparatus obtained by the volume data obtaining function 56. This function 57 resultantly generates the volume data L including voxels each having a value to which "true (1)" is set when the voxel position (x, y, z) corresponds to the cerebral infarction site and "false (0)" is set when the position does not correspond.

L(x, y, z)=(1 (true) if the (x, y, z) corresponds to the cerebral infarction site, 0 (false) if not)

This function further extracts a portion corresponding to cerebral parenchyma from the same volume data, and resultantly generates volume data B including voxels each having a value to which "true (1)" is set when the voxel position (x, y, z) corresponds to the cerebral parenchyma and "false (0)" is set when the position does not correspond.

B(x, y, z)=(1 (true) if the (x, y, z) corresponds to the cerebral parenchyma, 0 (false) if not)

The function performs a set operation using the volume data L and the volume data B, and generates volume data (B∧¬L) including voxels each having a value to which "1" is set when the data L has a value "0" and the data B has a value "1" at the voxel position, and "0" is set in the other cases.

$$(B \wedge \neg L)(x,y,z) = B(x,y,z)(1-L(x,y,z))$$

The amount of blood in normal brain tissue is substantially identical across the tissue. However, to speak more correctly, the amount is smaller in white matter and larger in gray matter. Volume data S where an image has been taken by an X-ray CT apparatus or an MRI apparatus without contrast medium, and visualized volume data T where an image has been taken with the contrast medium substantially uniformly distributing in the blood are then obtained. Volume data X representing the contrast medium concentration distribution in the brain is created from a difference image between the data T and the data S.

Here, the logical multiplication between $(B \wedge \neg L)$ and X on each voxel is assumed as follows.

$$U(x,y,z) = (B \wedge \neg L)(x,y,z)X(x,y,z)$$

U is substantially proportional to the contrast medium concentration distribution before restoration from cerebral infarction.

The logical multiplication between B and X on each voxel is assumed as follows.

$$V(x,y,z) = B(x,y,z)X(x,y,z)$$

V is approximately proportional to the contrast medium concentration distribution after complete restoration from cerebral infarction.

There is an easier method which does not consider the fact that in normal brain tissue, the amount of blood is smaller in the white matter and larger in the gray matter and assumes X to have a certain value everywhere. In this case, B, L and $(B \wedge \neg L)$ can be created on the basis of volume data taken by the X-ray CT apparatus and the MRI apparatus without using the contrast medium.

Simulation is made on what image is obtained in the case of X-ray imaging in the same direction as that in the case of imaging the object P, through calculation using U, which can generate an image (predictive first difference image) that predicts the first difference image (P2−M). An analogous process using V can generate an image (predictive second difference image) that predicts the second difference image (P3−M) in the case of complete restoration from cerebral infarction. On the basis of these predictive images, the predictive ratio image 90 (E) can be calculated.

E="predictive image for (P3−M)"/"predictive image for (P2−M)"

Next, an example of the operation of the X-ray diagnostic apparatus 10A according to this embodiment is described.

Figure 12:
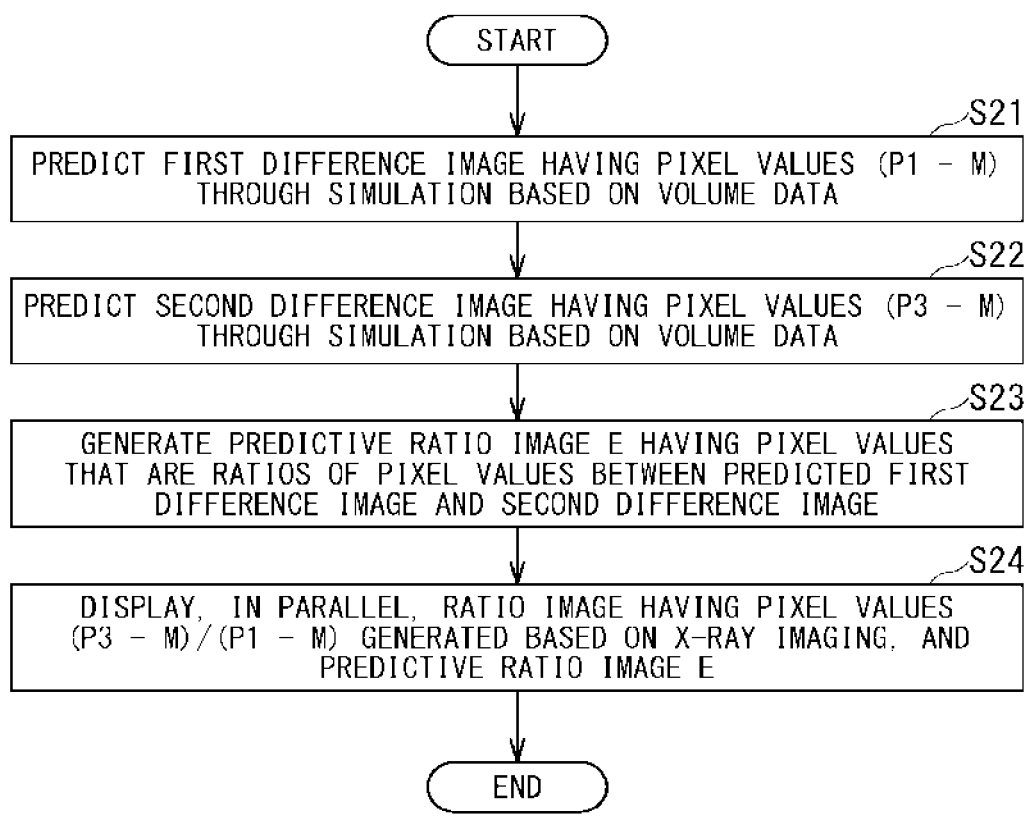
FIG. 12 is a flowchart showing an example of procedures for causing the predictive ratio image generating function and the second image generating function to display the ratio image and the predictive ratio image (E) on the display in parallel.

FIG. 12 is a flowchart showing an example of procedures for causing the predictive ratio image generating function 57 and the second image generating function 53A to display the ratio image 82 and the predictive ratio image 90 (E) on the display 42 in parallel. The procedures start after the ratio image 82 (see FIG. 7) is generated on the basis of the projection data obtained by X-ray imaging of the region of interest of the object P according to the series of procedures shown in FIG. 8.

In step S21, the predictive ratio image generating function 57 simulates what image is obtained in the case of X-ray imaging in the same direction as that in the case of imaging the object P, through calculation using the volume data U, which can thereby generate an image (predictive first difference image) that predicts the first difference image (P2−M).

Next, in step S22, the predictive ratio image generating function 57 simulates what image is obtained in the case of X-ray imaging in the same direction as that in the case of imaging the object P, through calculation using the volume data V, which can thereby generate an image (predictive second difference image) that predicts the second difference image (P3−M).

Next, in step S23, the predictive ratio image generating function 57 generates a predictive ratio image 90 (E) having pixel values that are the ratios between the pixels of the predictive first difference image and the pixels of the predictive second difference image.

In step S24, the second image generating function 53A displays the ratio image 82 generated on the basis of the projection data obtained by taking X-ray images of the region of interest of the object P (see FIG. 7), and the predictive ratio image 90 (E) generated by the predictive ratio image generating function 57, on the display 42 in parallel (see FIG. 11).

The above procedures can display the ratio image 82 and the predictive ratio image 90 (E) on the display 42 in parallel.

The X-ray diagnostic apparatus 10A including the image processing apparatus 12 according to the second embodiment can also exert advantageous effects equivalent to those of the X-ray diagnostic apparatus 10 according to the first embodiment.

The X-ray diagnostic apparatus 10A according to the second embodiment can generate the predictive ratio image 90 (E) that is the ratio image 82 predicted to be obtained in the case where the bloodstream obstruction has been completely removed, and display this image and the ratio image 82 on the display 42 in parallel. Consequently, the X-ray diagnostic apparatus 10A allows the user to easily identify the bloodstream restoration site and the degree of restoration. Furthermore, in the case of generating the comparison assistance image having pixel values that are each the difference of each pixel of the predictive ratio image 90 (E) and each pixel of the ratio image 82 and displaying this image on the display 42, the user can further easily identify the bloodstream restoration site and the degree of restoration.

Any one of the aforementioned embodiments can generate the image that allows easy identification of bloodstream recovery in the territory during or after thrombectomy using the catheter 34.

The processing circuitry in the above-described embodiments is an example of the processing circuitry described in the claims. In addition, the term "processor" used in the explanation in the above-described embodiments, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit and executing the programs.

In addition, programs may be directly installed in the circuit of a processor instead of storing programs in the memory circuit. In this case, the processor implements various types of functions by reading out programs stored in its own circuit and executing the programs. Moreover, each function of the processing circuitry may be implemented by processing circuitry configured of a single processor. Further, the processing circuitry may be configured by combining plural processors independent of each other so that each function of the processing circuitry is implemented by causing each processor to execute the corresponding program. When plural processors are provided for the processing circuitry, a memory circuit for storing the programs may be provided for each processor or one memory circuit may collectively store all the programs corresponding to all the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus generating an X-ray image in a region of interest, comprising: a radiography device configured to take a first X-ray image before injection of a contrast medium, and a second X-ray image and a third X-ray image after the injection of the contrast medium; and
processing circuitry configured to generate an output image having pixel values that are ratios of a difference between pixel values of the second X-ray image and the first X-ray image and a difference between pixel values of the third X-ray image and the first X-ray image;
generate a predictive output image after complete removal of a bloodstream obstruction, by
(i) predicting and generating a first difference image between the second X-ray image and the first X-ray image,
(ii) predicting and generating a second difference image, after a complete removal of a bloodstream obstruction, between the third X-ray image and the first X-ray image, and
(iii) generating the predictive output image having pixel values that are ratios of pixel values between the first difference image and the second difference image,
wherein the first difference image and the second difference image are predicted and generated through calculation using medical three-dimensional image data on the region of interest, and
wherein the predictive output image is generated after the complete removal of the bloodstream obstruction; and
display, in parallel on a display, the output image and the predictive output image.

2. The X-ray diagnostic apparatus according to claim 1, wherein the processing circuitry is further configured to
generate a comparison assistance image having pixel values that are ratios of the pixel values of the output image and the pixel values of the predictive output image; and
display the generated comparison assistance image on the display.

3. The X-ray diagnostic apparatus according to claim 1, wherein the processing circuitry is further configured to
cause the predictive output image to be from a viewpoint identical to that of the output image.

* * * * *